United States Patent [19]

Magney

[11] 4,180,162
[45] Dec. 25, 1979

[54] COMBINATION DISPENSER-DISPOSAL CARTRIDGE FOR A SURGICAL BLADE

[76] Inventor: Herbert C. Magney, 433 W. Linda La., Chandler, Ariz. 85224

[21] Appl. No.: 966,134

[22] Filed: Dec. 4, 1978

[51] Int. Cl.² .............................................. B65D 83/10
[52] U.S. Cl. .................................. 206/363; 206/356; 206/359; 30/40.2; 221/58
[58] Field of Search ............... 206/349, 356, 359, 363, 206/370; 30/40, 40.2, 123, 339; 221/29, 152, 40, 41, 58, 59, 270, 279, 232

[56] References Cited

U.S. PATENT DOCUMENTS

| | | | |
|---|---|---|---|
| 2,641,358 | 6/1953 | Santo | 206/359 |
| 2,653,704 | 9/1953 | Nelson | 206/355 |
| 2,684,151 | 7/1954 | Arrighi | 206/355 |
| 2,976,986 | 3/1961 | Linn | 206/356 |
| 3,244,317 | 4/1966 | Raybin | 221/58 |
| 3,941,243 | 3/1976 | Yamada | 206/356 |
| 4,120,397 | 10/1978 | Neumann | 206/356 |

*Primary Examiner*—Joseph Man-Fu Moy
*Attorney, Agent, or Firm*—William H. Drummond

[57] ABSTRACT

A cartridge for dispensing and disposing of a single surgical blade. The cartridge is specially adapted for machine loading of the blade. The cartridge includes an elongate open-top box with means for receiving and positioning the blade in a curved position to accept the mating boss of a scalpel handle. The box also includes means for stripping a used blade from the scalpel handle and retaining it within the box for disposal. A cover member for the open top of the box is provided. The cover member has downwardly projecting positioning studs which cooperate with mating recesses in the side walls of the box to position the cover on the open top of the box.

1 Claim, 17 Drawing Figures

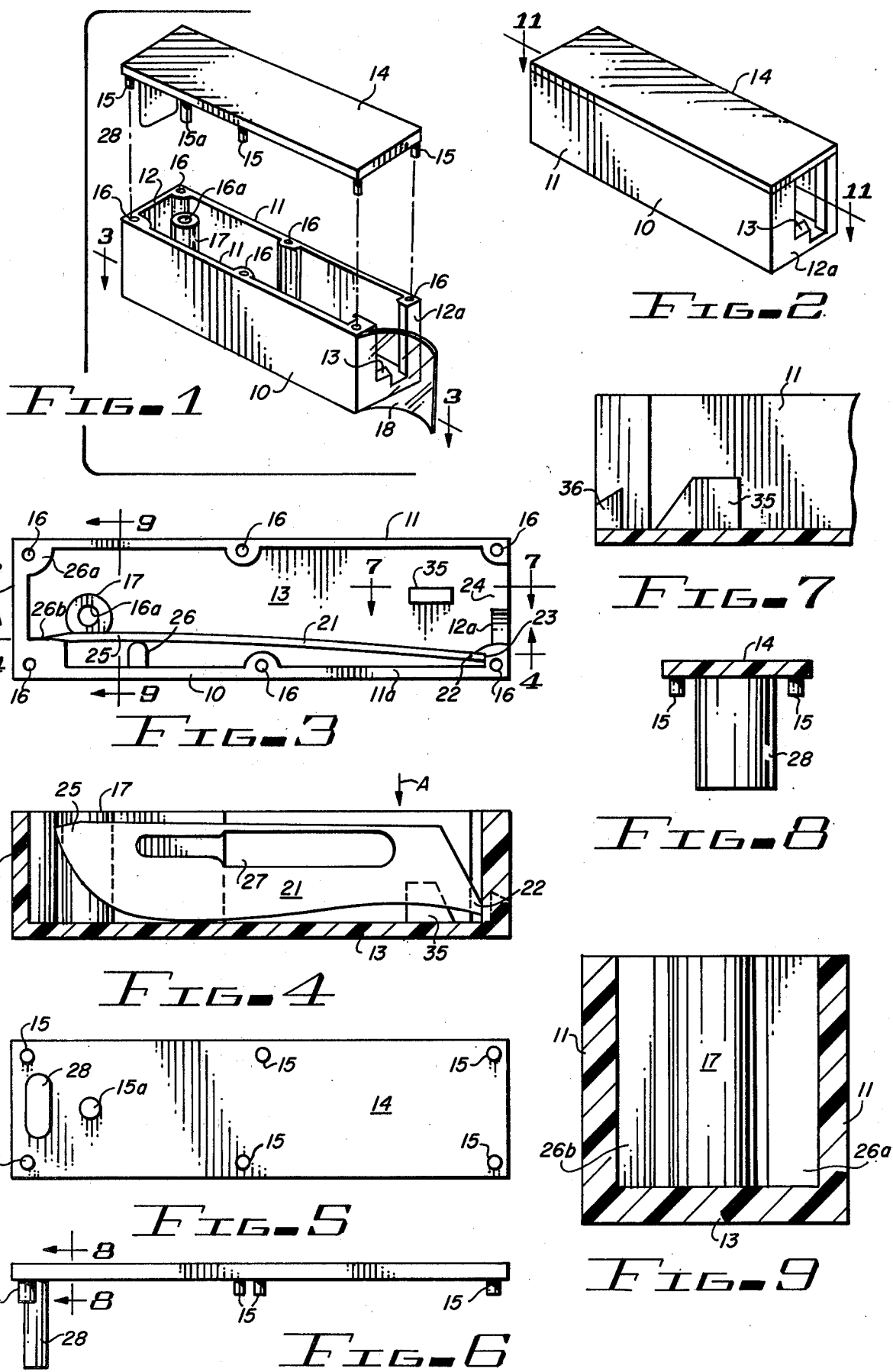

COMBINATION DISPENSER-DISPOSAL CARTRIDGE FOR A SURGICAL BLADE

This invention relates to a combination dispenser-disposal cartridge for a surgical blade and constitutes an improvement on the invention described in my issued U.S. Pat. No. 4,106,620 issued Aug. 15, 1978.

In my issued U.S. Pat. No. 4,106,620, I disclose a dispenser for storing at least one sharpened surgical blade, dispensing the blade and, according to a further embodiment, a dispenser which includes a separate compartment for separating used blades from a scalpel handle and storing them for disposal. While the invention disclosed in my issued patent functions efficiently for the purposes described therein, it has subsequently appeared highly desirable to provide a cartidge for more efficiently storing and dispensing a single blade which would also function as a disposal cartridge, specially adapted to receive and store a single used blade for disposal. Additionally, it has appeared desirable to provide a blade storage-dispensing and disposal cartridge which was more amenable to mass production of the cartridge itself and which is specially configured to permit machine loading of the new blades into the receptacle and to permit sealing of the receptacle to maintain sterile conditions therewith.

Accordingly, it is the principal object of the present invention to provide a combination dispenser-disposal cartridge for a single surgical blade.

Yet another object of the invention is to provide such a combination cartridge which is specially adapted for mass production by conventional plastic marketing techniques.

Yet another object of the invention is to provide such a combination dispenser-disposal cartridge which is specially adapted for machine loading of the surgical blade therewith.

These and other, further, and more specific objects and advantages of the invention will be apparent to those skilled in the art from the following detailed description thereof, taken in conjunction with the drawings, in which:

FIG. 1 is an exploded perspective view of a combination cartridge, constructed in accordance with the principals of the present invention;

FIG. 2 is a perspective view of the cartridge of FIG. 1 with the box and cover components fully assembled;

FIG. 3 is a sectional view of the box portion of the cartridge of FIG. 1 taken along section line 3—3 thereof, and showing a surgical blade positioned therewith;

FIG. 4 is a sectional view of the box portion of the cartridge of FIG. 3 taken along section line 4—4 thereof;

FIG. 5 is a plan view of the lower surface of the cover member of the cartridge of FIG. 1;

FIG. 6 is an elevation view of the cover member of FIG. 5;

FIG. 7 is a partial sectional view of the box member of FIG. 3 taken along section line 7—7 thereof;

FIG. 8 is a sectional view of the cover member of FIG. 6 taken along section line 8—8 thereof;

FIG. 9 is a sectional view of the box member of FIG. 3 taken along section line 9—9 thereof;

Figure 10A:
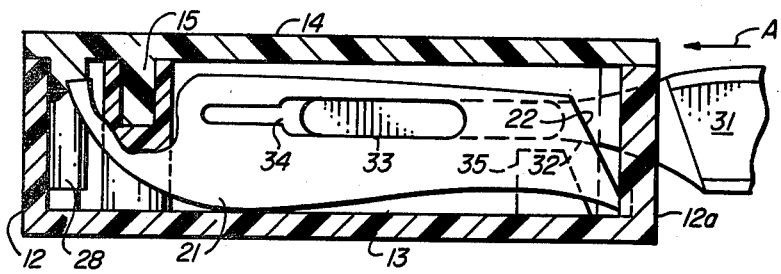
FIGS. 10A-10C are a series of sectional elevation views of the cartridge of FIG. 2 showing the sequence of steps involved in the engagement of a surgical blade with a scalpel handle.

At present, disposable surgical scalpel blades are commercially available in several sizes, produced by various manufacturers. They can be obtained commercially in sterile or non-sterile packaging. These blades are adapted to fit conventional metal scalpel handles of various sizes to form knives used for a variety of purposes in hospitals (surgery, pathology laboratories, etc.), in research laboratories and in science departments in various schools and universities.

The typical commercially available surgical blade has a sharpened tip and cutting edge portion and a shank portion extending rearwardly therefrom. The shank portion of the blade is provided with an elongate aperture which is shaped and adapted to receive a mating elongate boss formed on the forward or attaching tip of a scalpel handle.

The elongate handle-engaging aperture of the blade has a widened rear portion and a narrowed forward portion. The widened rear portion of the aperture initially receives the engaging boss of the scalpel handle and guides the boss forward into the narrowed forward portion of the aperture. The boss is undercut such that the edges of the narrowed forward portion of the aperture are engaged between the scalpel handle and the undercut surface of the boss. When the boss is completely inserted within the blade aperture, the rear edge of the blade aperture snaps under the undercut surface at the rear of the engaging boss, thus achieving locking engagement between the blade and the scalpel handle.

To remove the blade from the scalpel handle, the rear edge of the blade is lifted away from the handle to disengage the rear end of the blade aperture from the rear end of the boss. The blade is then pushed forward until the undercut boss clears the narrowed forward portion of the blade aperture, permitting the blade to be lifted completely clear of the handle.

Briefly, in accordance with the present invention, I provide a combination dispenser-disposal cartridge for a surgical blade. The cartridge is specially adapted for machine loading of the blade and comprises an elongate open-topped box including floor, side walls and end walls and having an aperture in one end wall. Blade-positioning means are formed integrally with the box portion and include a slot extending upwardly from the floor of the box alongside the aperture which is dimensioned to receive the shank end of a surgical blade and blade tip holding members extending upwardly from the floor of the box which are spaced apart to receive and frictionally engage the tip and at least a portion of the cutting edge of the blade. The slot and blade tip holder cooperate to position the blade such that the shank portion thereof curvingly extends from the tip rearwardly to the shank. A cover member is provided having downwardly projecting positioning studs which cooperate with mating recesses in the side walls of the box to position the cover on the open top of the box member. The cartridge also includes members which cooperate to strip a used surgical blade from the scalpel handle and retain the blade within the cartridge for disposal. These blade stipping elements include a single member extending upwardly from the floor of the box, intermediate the side walls thereof, for urging the shank end of the used blade away from the scalpel handle and for stripping the blade from the boss of the scalpel handle as the handle is withdrawn from the aperture, and an abutment shoulder formed in the lower edge of the aperture for contacting the lower rear edge of the blade as it is stripped from the scalpel handle boss, to retain the blade within the box when the scalpel handle is withdrawn.

Turning now to the drawings, in which like reference characters denote the same elements in the several views, FIGS. 1 and 2 depict, respectively, exploded and assembled views of a combination surgical blade dispenser-disposal cartridge which includes a lower box portion generally indicated by reference numeral 10 which includes side walls 11, and walls 12 and a floor 13. The box portion 10 is provided with a cover member 14. The cover 14 has integral downwardly extending positioning studs 15 which cooperate with mating recesses 16 formed in the side walls 11 of the box 10 to position the cover 14 on the open top of the box 10, forming the complete enclosure which constitutes the blade dispensing-disposal cartridge of the invention. If desired, additional positioning studs such as the stud 15A can be provided which mate with corresponding recesses such as the recess 16A formed in an upstanding post 17 which is part of the blade tip holding means, to be described later. The downwardly projecting studs 15 and 15A of the cover member 14 are preferably of of slightly larger diameter than the mating recesses 16 and 16A so as to insure a snug press-fit between the cover 14 and the box portion 10 when the cartridge is fully assembled. To insure complete sterility of the contents of the cartridge, the cover 14 and the box portion 10 are preferably formed of a thermo-plastic material and these components are heat-sealed during the assembly thereof and a pressure-sensitive foil flap 18 is provided to seal the aperture in the end wall 12A of the box member 10.

The box member 10 is formed with an open top as shown in FIG. 1 in order to facilitate machine loading of surgical blades into the cartridge as shown in FIGS. 3-4. The surgical blade 21 is simply inserted downwardly in the direction of the arrow A in such fashion that the tip 22 of the shank portion of the blade is received in a slot 23 formed in the side wall 11A of the box 10 adjacent the aperture 24 formed in end wall 12A. The tip 25 of the blade 21 is received between abutments 26 formed in side wall 11A and the pillar 17. The abutments 26 and the pillar 17 are positioned such that when the shank tip 22 of the shank portion of the blade 21 is received in the slot 23, the blade curvingly extends from the forward tip 25 toward the shank tip 22, to facilitate insertion of the boss of a scalpel handle into the slot 27 formed in the blade 21, as will be described more fully below.

After insertion of the blade 21 into the box portion 10 as shown in FIGS. 3-4, the cover 14 is affixed to the box portion 10 by aligning the positioning studs 15 and 15A with the mating recesses 16 and 16A, and pressing the cover 14 into engagement with the tops of the side walls 11 of the box portion 10. The cover 14 also has a downwardly projecting member 28 which is received between the abutments 26 and 26A formed in the end wall 12 of the box portion 10 (as shown in FIG. 9). The purpose of the depending member 28 will be explained below.

Figure 10B:
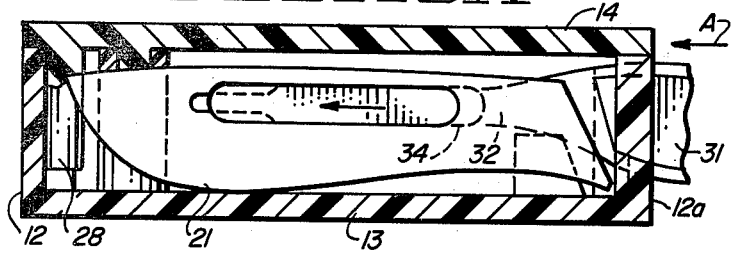
Figure 10C:
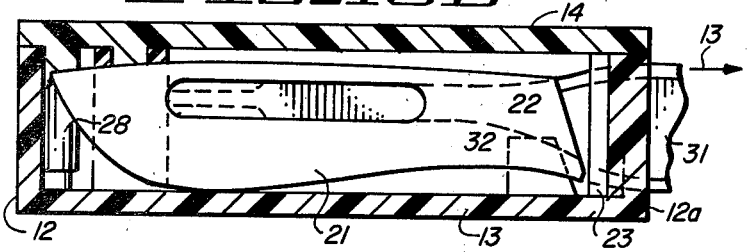
Figure 11A:
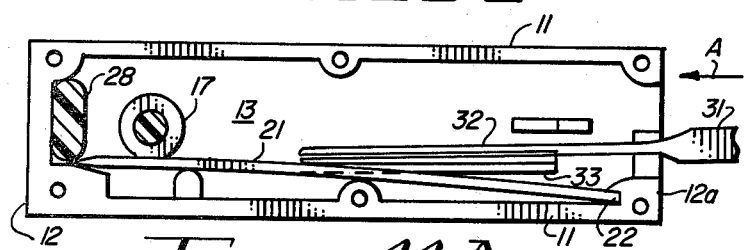
FIGS. 11A-11C are a series of sectional plan views corresponding to the elevation views of FIGS. 10A-10C.
Figure 11B:
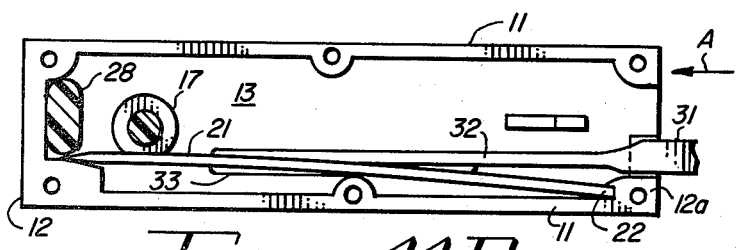
Figure 11C:
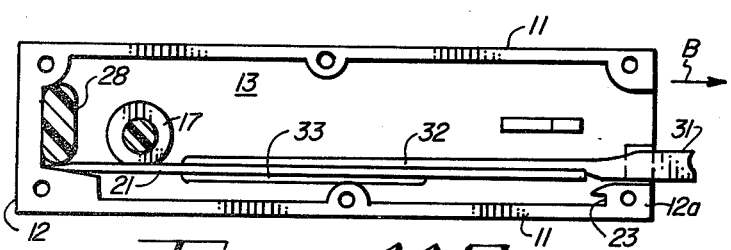

The steps in withdrawing a surgical blade from the cartrige of FIGS. 1-9 are illustrated in FIGS. 10A-10C and 11A-11C. The scalpel handle 31 has a narrowed forward portion 32 on which is located an undercut blade engaging boss 33. The boss 33 is undercut such that the edges of the narrowed forward portion of the aperture 34 of the blade are engaged between the narrowed portion of the scalpel handle 32 and the undercut surface of the boss 33. The handle 31 is inserted through the aperture in the end wall 12A of the cartridge 10 and the boss 33 is received within the enlarged rear portion of the slot 34 in the blade 21. The handle 31 is moved forward within the cartridge in the direction of the arrows A, as shown in FIGS. 10B and 11B, until the forward narrowed portion of the aperture 34 in the blade 21 is engaged between the boss 33 and the handle 32, as shown in FIGS. 10C and 11C. At this point, the blade 21 has been moved forward within the cartridge 10 to the point that the rear edge 22 of the blade 21 is unseated from the vertical slot 23 formed in the side wall of the cartridge 10 next to the aperture in the end wall 12A. When the rear edge 22 of the blade 21 clears the edge of the slot 23, the blade snaps into its operative position on the scalpel handle, as shown in FIGS. 10C and 11C, and the blade is withdrawn from the cartridge 10 by moving the handle rearwardly in the direction of the arrows B.

Figure 12A:
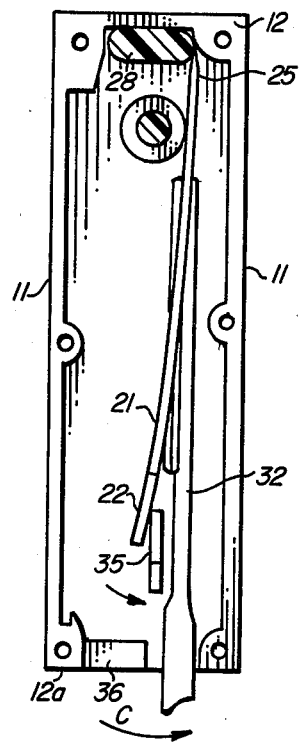
FIGS. 12A-12B are a series of sectional plan views of the cartridge of FIG. 2 showing the steps of stripping a used blade from a scalpel handle for disposal with the cartridge.
Figure 12B:
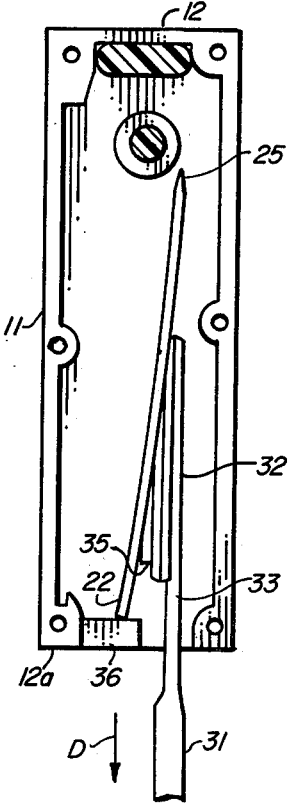

Removal of a used blade from a scalpel handle and storage of the blade within the cartridge 10 is accomplished as shown in FIGS. 12A and 12B. The scalpel handle 31 with the blade attached is inserted into the aperture in the end wall 12A of the cartridge 10 until the tip 25 of the blade 21 is engaged between the downwardly projecting boss 28 and the rounded internal corner between the end wall 12 and side wall 11 of the box portion, as shown in FIG. 12A. At this point, the handle 31 is moved to the right, as indicated by the arrow C, and the rear edge 22 of the blade 21 is stripped away from the narrowed forward portion 32 of the scalpel handle 31 by engagement against the upstanding blade disengaging projection 35 formed integrally with the floor 13 of the box portion 10. Next, movement of the scalpel handle 31 to the rear, as indicated by the arrow D (FIG. 12B) carries the blade 21 to the rear until the rear edge 22 of the blade 21 contacts a shoulder 36 formed along the leftmost portion of the aperture in the end wall 12A and extending upwardly a distance sufficient to engage the rear edge 22 of the blade 21 and retain the blade 21 within the cartridge. Continued movement of the handle 31 in the direction of the arrow D disengages the narrowed forward portion 32 from the slot 34 formed in the blade 21, leaving the blade within the cartridge for disposal.

As will be observed from FIGS. 10, 11 and 12, the surgical blade can be attached to the scalpel handle and then detached therefrom without the necessity for touching the blade by hand, thereby permitting the operation to be conducted with increased safety and with less chance of contaminating the blade, which is particularly important in surgical operations.

Having described my invention in such terms as to enagle those skilled in the art to understand and practice it, and having identified the presently preferred embodiments thereof, I claim:

1. A combination dispenser-disposal cartridge for a surgical blade, specially adapted for machine-loading of said blade therein, comprising:
   (a) means defining an elongate open-topped box portion including floor, side walls and end walls and having an aperture in one end wall thereof;
   (b) blade-positioning means formed integrally with said box portion, including
      (i) means defining a slot extending upwardly from the floor of said box along a side of said aperture, said slot being dimensioned to receive the shank end of a surgical blade, and
      (ii) blade tip holding means comprising at least two members extending upwardly from the floor of said box and spaced apart to receive and frictionally engage the tip and at least a portion of the cutting edge of said blade therebetween,
   said slot and blade tip holder cooperating to position said blade such that the shank portion thereof curvingly extends from the tip rearwardly to the shank portion thereof;
   (c) a cover member for the open top of said box portion having downwardly projecting positioning studs which cooperate with mating recesses in the side walls of said box member to position said cover on the open top of said box member;
   (d) blade stripping means for separating a used surgical blade from a scalpel handle, including
      (i) a finger member extending upwardly from the floor of said box portion intermediate the side walls thereof for urging the shank end of said blade away from said scalpel handle and for stripping said blade from the boss thereof as said scalpel handle is withdrawn from said aperture, and
      (ii) an abutment shoulder formed in the lower edge of said aperture for contacting the lower rear edge of said blade as it is stripped from said scalpel handle boss and for retaining said blade within said box portion when said scalpel handle is withdrawn therefrom.

* * * * *